(12) United States Patent
Scholten et al.

(10) Patent No.: US 10,368,875 B2
(45) Date of Patent: Aug. 6, 2019

(54) SURGICAL CLIP

(71) Applicant: Aesculap AG, Tuttlingen (DE)

(72) Inventors: Thomas Scholten, Tuttlingen (DE);
Gunnar Wanke, Kreuzlingen (CH);
Erick Drost, Obendorf a. N. (DE)

(73) Assignee: Aesculap AG (DE)

(*) Notice: Subject to any disclaimer, the term of this patent is extended or adjusted under 35 U.S.C. 154(b) by 379 days.

(21) Appl. No.: 15/306,633

(22) PCT Filed: Apr. 24, 2015

(86) PCT No.: PCT/EP2015/058944
§ 371 (c)(1),
(2) Date: Oct. 25, 2016

(87) PCT Pub. No.: WO2015/165820
PCT Pub. Date: Nov. 5, 2015

(65) Prior Publication Data
US 2017/0042545 A1    Feb. 16, 2017

(30) Foreign Application Priority Data
Apr. 28, 2014    (DE) .......................... 10 2014 207 955

(51) Int. Cl.
*A61B 17/122*    (2006.01)
*B21D 7/00*    (2006.01)
(Continued)

(52) U.S. Cl.
CPC .............. *A61B 17/122* (2013.01); *B21D 7/00* (2013.01); *A61B 2017/00526* (2013.01); *A61B 2017/12004* (2013.01); *B21D 11/20* (2013.01)

(58) Field of Classification Search
CPC ........ A61B 17/122; A61B 2017/00526; A61B 2017/12004; B21D 7/00; B21D 11/20
See application file for complete search history.

(56) References Cited

U.S. PATENT DOCUMENTS

| | | | |
|---|---|---|---|
| 5,217,473 A * | 6/1993 | Yoon ................ | A61B 17/12013 606/141 |
| 5,441,509 A | 8/1995 | Vidal et al. | |

(Continued)

FOREIGN PATENT DOCUMENTS

| | | |
|---|---|---|
| CN | 101606856 A | 12/2009 |
| CN | 102988095 A | 3/2013 |

(Continued)

OTHER PUBLICATIONS

International Search Report and Written Opinion of the International Searching Authority for International Application No. PCT/EP2015/058944, dated Mar. 11, 2016, 15 pages.

(Continued)

*Primary Examiner* — Phong Son H Dang
(74) *Attorney, Agent, or Firm* — RatnerPrestia

(57) ABSTRACT

A surgical clip for a surgical clip applicator includes at least one pair of clip arms. Each clip arm has a distal end and a proximal end. The two clip arms are connected to each other at the proximal ends of the clip arms and form a clip throat. A tangent angle between a tangent to a neutral fiber of a clip arm and a perpendicular to a longitudinal axis of the clip increases over the entire length of the clip arm substantially continuously.

16 Claims, 6 Drawing Sheets

(51) Int. Cl.
    *A61B 17/00*      (2006.01)
    *B21D 11/20*      (2006.01)
    *A61B 17/12*      (2006.01)

(56) References Cited

U.S. PATENT DOCUMENTS

| | | | |
|---|---|---|---|
| 5,713,911 A | 2/1998 | Racenet et al. | |
| 6,015,417 A * | 1/2000 | Reynolds, Jr. | A61B 17/064 606/151 |
| 6,226,843 B1 | 5/2001 | Crainich | |
| 6,417,758 B1 * | 7/2002 | Russell | H01H 37/043 165/80.1 |
| 8,137,351 B2 * | 3/2012 | Prandi | A61B 17/0682 606/75 |
| 9,585,674 B2 | 3/2017 | Terada | |
| 2006/0100649 A1 * | 5/2006 | Hart | A61B 17/0643 606/157 |
| 2006/0212049 A1 * | 9/2006 | Mohiuddin | A61B 17/083 606/151 |
| 2007/0173866 A1 | 7/2007 | Sorrentino et al. | |
| 2008/0045981 A1 * | 2/2008 | Margolin | A61B 17/122 606/151 |
| 2008/0312670 A1 * | 12/2008 | Lutze | A61B 17/122 606/157 |
| 2011/0224701 A1 | 9/2011 | Menn | |
| 2011/0295290 A1 | 12/2011 | Whitfield | |
| 2012/0048759 A1 | 5/2012 | Disch et al. | |
| 2013/0072947 A1 | 3/2013 | Terada | |
| 2014/0343581 A1 * | 11/2014 | Lee | A61B 17/083 606/151 |

FOREIGN PATENT DOCUMENTS

| | | |
|---|---|---|
| DE | 69322680 T2 | 6/1999 |
| DE | 102009018820 A1 | 10/2010 |
| DE | 202010008714 U1 | 1/2011 |
| EP | 0567965 A2 | 11/1993 |
| EP | 0576835 A2 | 1/1994 |
| EP | 1810622 A1 | 7/2007 |
| EP | 2389878 A1 | 11/2011 |
| EP | 1810622 B1 | 2/2012 |
| JP | H05022577 A | 1/1993 |
| JP | 2009523044 A | 6/2009 |
| JP | 2013063107 A | 4/2013 |
| WO | 2007087834 A1 | 8/2007 |
| WO | 2012135141 A2 | 10/2012 |

OTHER PUBLICATIONS

Erich Drabbe: "Stanztechnik" Erster Teil, Schnittechnik, Technologie des Schneidens, Jan. 1, 1940, Springer-Verlag Gmbh, with translation 2 pages.
German Search Report for German Application No. 10 2014 207 955.1, dated Mar. 11, 2015 with translation, 15 pages.
Chinese Office Action for Chinese Application No. 201580023560.1, dated Aug. 2, 2018 with translation, 19 pages.
Notification of Reason for Rejection for Japanese Application No. 2016-564215, dated Jan. 29, 2019, with translation—12 pages.

\* cited by examiner

SURGICAL CLIP

RELATED APPLICATION(S)

This is the U.S. National Phase of International Application No. PCT/EP2015/058944, filed Apr. 24, 2015, which is related to and claims the benefit of priority of German Application No. DE 10 2014 207 955.1, filed Apr. 28, 2014. The contents of International Application No. PCT/EP2015/058944 and German Application No. DE 10 2014 207 955.1 are incorporated by reference herein in their entireties.

FIELD

The invention relates to a surgical clip. In particular, the invention concerns a surgical clip which has an advantageous compression force progression in a compressed state, i.e. when tissue is held together or pressed between the clip arms.

BACKGROUND

Several surgical clips are known in the art. Applied Medical distributes a surgical clip called EPIX Universal CA500 which has the two substantially straight clip arms connected to each other via a substantially V-shaped portion. The two straight clip arms run essentially in parallel to the longitudinal axis of the surgical clip, and relatively small bending radii are formed in the transient regions between the clip arms and the connection portion as well as at the throat of the connection portion. This means that the transient regions are formed by breaks. Comparable surgical clips with comparable geometry are distributed also by United States Surgical, labeled Endo Clip Autosuture 5 mm, and by Ethicon, labeled Ligamax 5.

The Endo Clip Autosuture III 5 mm, which is distributed by Unites States Surgical as well, has a somewhat different geometry. This clip also comprises two substantially straight and parallel clip arms, and a connection portion for the two straight clip arms which is formed with a throat having a smallish radius of curvature. In contrast to the previously described surgical clips, the transient regions between the clip arms and the connection portion are formed with a distinctly larger radius of curvature, and thus rather as bent portions than as broken portions.

A patent application U.S. 2011/0224701 A1 discloses a surgical clip having a semicircular outer surface and a profiled inner surface. The semicircular outer surface serves to prevent blocking of the clip in the jaw part of the clip applicator, and the profiled inner surface is to improve the grip on the clamped tissue. In a side view, the clip arms of the clip respectively have straight portions which run parallel to each other in the region of the distal end of the clip, i.e. at its open side. Besides, the clip arms consist of plural and substantially indeformable sections which are interconnected by deformable sections.

All known clips have in common that each clip arm has a substantially straight portion, and that the connection portion has two substantially straight portions. Then, more or less curved portions are formed in the throat and in the transient region between the clip arm and the connection portion. Besides, all of these clips are single rack clips, i.e. clips that can be bent from a piece of wire and substantially extend in a plane (aside from the wire bead).

A problem with this kind of clips resides in that they exhibit unfavorable performance upon application, i.e. upon pressing or compressing by means of a clip applicator. On the one hand, due to the formation of the smallish radius of curvature in the transient region from the clip arm to the connection portion, a region is created in which the material of the clip (a metal such as titanium or titanium alloys) is stretched more than in the adjacent regions which, resulting in that this region, which is in the following referred to as a break, cannot completely be deformed back into a straight form upon compressing the clip with an applicator. Thus, a spot remains in the compressed clip at which the two clip arms are spaced farther away from each other. This leads to a suboptimal closure of the respectively clipped, i.e. pinched, vessel.

A further problem of this kind of clips resides in that the barring of these clips in the compressed state is weak at the distal ends of the clip arms. This means that a force that leads to a barring of the vessel is barely applied onto the vessel at the distal clip ends. During the compression process the two parallel clip arms are deformed inwardly around the throat of the clips. Thereby, only the break and the transient region, respectively, of the clip remain in contact with the respective limb of the clip applicator. The break between the clip arm and the connection portion is bent open only when the distal ends of the clips touch each other (if no tissue is seized) or become on both sides applied to the tissue to be seized (if tissue is seized). Thereby, the distal ends of the clip arms deform to the outside, and the relevant force transmission point into the tissue relocates toward the break. This in turn relieves the distal ends of the clip arms, and they relieve their elastic deformation (substantially while maintaining their current position). Now, if the break in the clip arm has been deformed back as far as possible, i.e. the clip is completely compressed, this results in that the clip can hardly muster any further barring force and compression force, respectively, because the distal ends are easily and elastically deformable to the outside and because there are locations in the middle portion of the clip where the clip arms touch each other (if no tissue is seized) or the clip arms apply on both sides of the seized tissue substantially punctiformly (in the following, this region will be referred to as a middle contact region in both cases). Namely, in this manner, the distal ends have been completely relieved toward the end of the compression process, when the break in the clip arm has been deformed back with a force by far exceeding the force being required to bring the remaining regions of the clip into the compressed form of the clip. The compression force, which should technically be distributed as uniformly as possible over the length of the compressed clip, then concentrates on the vicinity of the clip throat and the middle contact region of the clip.

It is an object of the invention to provide a surgical clip in which a uniform and as small as possible gap forms between the clip arms, and in which the clip arms deliver a sufficient compression force to the point of their distal end. A further object of the invention resides in providing a surgical clip which exercises a uniform force onto the seized tissue over substantially the entire clip length. A still further object of the invention is to provide a manufacturing method for such a clip.

Definition of Terms

A clip has a non-compressed initial state and a compressed final state. Normally, tissue is located in the compressed state between two mating clip arms, such as a hollow organ like a blood vessel. In this case, the thickness and the consistency of the blood vessel wall determine the width of the gap between the clip arms in the compressed state. For this reason, specifications of the gap thickness of the clip in the compressed state herein always refer to the case that no tissue is located between the clip arms, because only then a meaningful comparison with the clips known from the art is possible. For this purpose, it can be set forth that the quality of a gap of the clip in the compressed state without any tissue located in-between give a clear indication toward the quality of the gap with tissue located in-between. The quality of the gap is also determined by the gap width and by the compression force applied by the clip arms along the clip arms. For example, if in a clip, without any tissue laying in-between, a parallel gap is formed which has a substantially equal compression force over its substantially entire length, a substantially equal compression force over the substantially entire length of the tissue-clip-contact line/area would result in the same clip with tissue laying in-between.

A clip consists of an even number of clip arms, of which respective two are associated with each other and form a plane. In this manner, plural substantially parallel planes are formed in case of plural clip arm pairs. The clip plane is a plane which runs in parallel to the planes described above and which substantially bisects the clip in the direction perpendicular to this plane. In each case, a pair of mating clip arms is connected at its proximal ends and forms a clip throat in the connection portion. The longitudinal axis of a clip or a pair of clip arms is a line extending from the clip throat to the middle between the two distal ends of the respective clip arms. This longitudinal axis (chain dotted line) runs proximally-distally.

The clip length L is the distance from the outside of the clip throat to the vertical projection of the distal ends of the clip arms onto the longitudinal axis of the clip, the clip width B is the distance of the outsides of the distal ends of two mating clip arms (i.e. these two clip arms form together a pair of clip arms), and the clip height H is the extension of the clip in a direction perpendicular to the clip plane. The clip length L, the clip width B and the clip height H refer to the outer dimensions of the respective clip.

The clear, or usable, clip length $L_1$ is the distance from the inside of the clip throat to the vertical projection of the distal ends of the clip arms onto the longitudinal axis of the clip, the clear, or usable, clip width $B_1$ is the distance of the inner sides of the distal ends of two mating clip arms (i.e. these two clip arms form together a pair of clip arms), and the clear, or usable, clip height $H_1$ is the distance of two adjacent clip arms, which together do not form a pair of mating clip arms. The clear clip length $L_1$, the clear clip width $B_1$ and the clip height $H_1$ refer to the inner dimensions of the respective clip.

The clip arm length l is the length of the unwinding of one clip arm into a line, wherein the clip arm length l refers to the neutral fiber (dashed line) of the clip arm. The neutral fiber is the geometric location of the centers of the moments of inertia along the respective clip arm. The length on the clip arm $l_a$ is indicated in percent (%), wherein a length on the clip arm of 0% corresponds to the clip throat, i.e. the location where the neutral fiber of the clip arm and two mating clip arms, respectively, intersect the longitudinal axis of the clip, and a length on the clip arm of 100% corresponds to the distal end of the respective clip arm. In a ring clip made of a sheet metal, the clip arm width b corresponds to the distance of the side edges of a clip arm. In a ring clip made of a sheet metal, the clip arm height h corresponds to the thickness of the sheet metal. When the clip arm width and/or the clip arm height is/are variable over the clip arms, various and variable clip arm widths and heights b', b'', h' may be present. The tangent angle α is the angle a tangent to the neutral fiber of the respective clip takes with a line standing vertically on the longitudinal axis of the clip. The tangent angle α is, thus, always between 0° and substantially 90°. In the following and unless stated otherwise, the description of the clip refers to the uncompressed state of the clip, in which the same is strainless.

On the one hand, the term of the surgical tubular shaft instrument comprises in this application endoscopic instruments, such as endoscopic clip applicators. On the other hand, this term also comprises surgical instruments for an open operation in which the functional portion and the effective portion, respectively, of the instrument is separated from the actuation portion and the handle portion, respectively, by a shaft or a shaft-like component. Here, the term shaft and shaft-like component, respectively, designates a component whose dimensions and location vis-à-vis the actuation portion (e.g. a handle) are substantially invariable during an actuation of the surgical instrument. An axial displacement along the axis of the shaft or shaft-like component and a torsion across or around this axis is thereby allowable, however a substantial displacement vis-à-vis this axis such that the two ends of the component substantially depart from this axis is not allowable. Preferably, the length of a shaft or shaft-like component is larger than the two other dimensions (width, depth) thereof, and further preferably, it is formed in a slim manner. Thereby, the shaft and the shaft-like component, respectively, need not to be round, closed, tubular or thin walled. It is decisive here that it is about an instrument which, unlike ordinary scissors, does not have a pivotal point around which all essential constituents of the instrument turn, but in which the force to open and close the jaw part is transferred via a relative axial movement of a component vis-à-vis the shaft.

In this application, the functional portion and the effective portion, respectively, is the region of the surgical tubular shaft instrument in which the actual function thereof is carried out. In a needle holder, it is the region seizing and holding the needle, i.e. the distal regions of the limbs. In scissors, it is the region that cuts the tissue or something other, i.e. the region at which the two shearing edges that glide past each other are formed. In a clip applicator, it is the region in which the clip is initially held while it is brought to the proper location and in the proper position by the surgeon, and in which the clip is subsequently administered, i.e. compressed. In other instruments, the definition of the functional portion and the effective portion, respectively, is to be applied correspondingly.

The effective range is the region of a singular limb in which the limb effects the intended function of the instrument, i.e. a gripping area in a needle holder, a shearing edge in scissors, and an application region of the clip.

Here, a closing and a closing operation, respectively, of the jaw part means that the effective ranges of the limbs typically move toward each other during the closing operation. In the case of scissors, the effective ranges of the limbs, i.e. the shearing edges, move past each other, and thereby apart from each other again, during the later course of the closing operation. This entire process is nevertheless referred to as a closing operation of the jaw part. In general terms, a closing operation designates the performance of the function assigned to the instrument, such as a seizing of tissue or for example a needle, a cutting of tissue or other matter, an administration of a clip or a spreading of tissue or other objects such as a clip. A subsequent opening and a subsequent opening operation, respectively, then designates the return of the limbs and, thus, also of the effective ranges and the distal regions, respectively, of the limbs of the jaw part of the respective instrument, to their initial position. In a surgical spreader, the assignment is just opposite because it performs its task when the limbs substantially move away from each other, i.e. carry out an opening operation, whereas a returning of the limbs to the initial position corresponds to a closing operation. Nevertheless, also in such an instrument there is a clear opening operation and a clear closing operation.

SUMMARY

The object of the invention is accomplished by a clip and by a manufacturing method as described herein.

According to an embodiment of the invention, there is disclosed a surgical clip for a surgical clip applicator having at least one pair of clip arms, wherein each clip arm has a distal end and a proximal end. The two clip arms of a pair of clip arms are connected to each other at their proximal ends to form a clip throat. Typically, the clip arms of a pair of clip arms are formed integrally and thus materially connected. In principle, the clip arms can also be formed individually and subsequently be connected to each other by e.g. welding. A tangent angle between a tangent to a neutral fiber of a clip arm and a perpendicular to a longitudinal axis of the clip continuously increases over substantially the entire length of the clip arm. This means that each clip arm has a continuously bent shape. Here, it does not depend on whether there are no straight sections on a clip arm at all because a curvature can also be approximated by a correspondingly fine structured polygonal line. It is, however, essential that no clearly perceivable series of straight sections and breaks is present.

Such a surgical clip having the shape of a continuous arc has the advantage that the tissue which is seized by the clip experiences a more uniform and higher force transmission after compressing than is possible using the clips known in the art. A surgical clip consisting of a series of straight portions and breaks, as is frequently the case in the prior art, renders a non-uniform distribution of the force applied to the seized tissue. This is due to the fact that more force is passed from the clip applicator into the clip at the breaks because these breaks form the main contact points with the inner surface of the jaw of the clip applicator. In the clips Endo Clip Autosuture 5 mm, Endo Clip Autosuture III 5 mm und EPIX Universal CA500, force is passed from the clip applicator into the clip almost solely at the outsides of the breaks over the entire process of compressing the clip. A force is passed in along the clip arms merely at the very beginning of the compressing operation, but as soon as the clip throat is deformed, the distal ends of the clips detach themselves from the clip applicator. Besides, the breaks are stiffer than other sections of the clip due to the cold plastic deformation upon generation of the same. In order to deform these breaks back into a straight section, which is necessary to obtain a uniform clip gap, an excessive force must be introduced into the clip. Thereby, the distal ends of the clip contact the tissue early, and are thereby deformed to the outside. Partly, even a plastic deformation toward the outside occurs thereby which is in no case desired and has a very negative impact on the closing force of the clip in the distal region. In the clip shape according to the invention, only an elastic deformation of the distal clip ends toward the outside occurs, if any, so that the maximum possible closing force is maintained also in the distal region. Besides, no breaks need to be deformed back.

In an advantageous embodiment of the invention, the tangent angle has, on a length on the clip arm of 6%, a value not exceeding 40°, preferably a value preferably not exceeding 30°, and further preferably a value of 20° to 30°. A surgical clip is subject to a wide variety of constraints. On the one hand, it shall have an opening width as large as possible so that also thick tissue or a thick vessel can be seized. For this purpose it needs to have a corresponding opening width not only at the distal end, but also in its proximal region, so that the tissue and the vessel, respectively, can be completely and as far as required, respectively, accommodated in the clip prior to a compressing operation. On the other hand, the clip shall also be as small as possible so that it can be applied in an endoscopic application using as thin as possible endoscopic applicators. The clip arms shall be as stiff as possible in order to securely hold together the seized tissue and to securely pinch off a seized vessel. On the other hand, the arms shall not be unnecessarily stiff because this in turn requires stiffer components in the applicator which is opposed to the desire for increasingly slim applicators. In order for the clip to obtain a shape that allows a uniform and sufficient force transmission onto the tissue to be seized, the tangent angle takes, on a length on the clip arm of 6%, a value not exceeding 40°, preferably a value preferably not exceeding 30°, and further preferably a value of 20° to 30°. In case of larger angles at this position on the clip arm, break-like regions would otherwise have to be formed along the clip arm in order to allow for a complete closure of the clip. Such break-like regions however result in the problems described above with respect to the non-uniform force transmission onto the tissue to be seized. In order to form a sufficiently large opening in the clip, so as to be able to accommodate the tissue to be seized before the clip is compressed, this angle shall not be larger at 6% length on the clip arm. In case of larger tangent angles at this position, it cannot always be ensured that the tissue to be seized can be placed in the clip. In particular when the tangent angle is in a range of 20° to 30°, the tissue can be introduced well into the clip and the clip can be pushed well onto the tissue. At the same time, a uniform closing force can be safeguarded by such a clip.

According to a further advantageous embodiment of the invention, the tangent angle has, on a length on the clip arm of 15%, a value of at least 58°, preferably a value of 58° to 75°. Using a tangent angle of at least 60° at this position can ensure that the curvature of the clip arm over the remaining length on the clip arm up to the distal end of the clip arm need not be formed too large so that regions similar to breaks would form and would lead to a non-uniform gap in the compressed clip. Using a maximum tangent angle of 75° at this position can ensure that a sufficient curvature in the clip arm can still be provided also distally of this position so that this distal region is deformed elastically in the lateral direction in the compressed state in order to exert a sufficient force onto the seized tissue.

According to another advantageous embodiment of the invention, the tangent angle has, on a length on the clip arm of 22%, a value of at least 60°, preferably a value of at least 67°, and further preferably a value of 67° to 80°. With this limitation, a still more uniform force transmission onto the seized tissue is achieved in the compressed state of the clip.

According to another advantageous embodiment of the invention, the tangent angle has, on a length on the clip arm of 27%, a value of at least 65°, preferably a value of at least 72°, and further preferably a value of 72° to 85°. With this limitation, a still more uniform force transmission onto the seized tissue is achieved in the compressed state of the clip.

According to another, further advantageous embodiment of the invention, the tangent angle has, on a length on the clip arm of about 0%, a value not exceeding 5°, and preferably a value of substantially 0°. This means that the clip throat forms no or only a very small break. This distinguishes the clip according to the invention from almost all earlier surgical clips and makes sure that the clip throat is heavily plastically deformed upon compression. From this plastic deformation, the clip according to the invention obtains the compression force which it applies to the seized tissue over the entire length of the clip arm. It is clear that in practice not absolute breaks will form but always curved sections develop. The above formulation is to clarify that no break is formed in the clip throat but that the clip traverses the clip axis substantially perpendicularly in the region of the clip throat.

According to a further advantageous embodiment of the invention, the tangent angle has, on a length on the clip arm of 100%, a value not exceeding 88°, and preferably a value of 80° to 88°. This configuration leads to the clip abutting with its distal ends against the clip applicators in the non-compressed state, and also the force being passed in there at the beginning of the compression operation. The force transmission point then relocates due to the plastic deformation of the clip arms toward proximal but without the distal ends of the clip arms detaching from the clip applicator at the beginning of the compression. This means that the distal ends of the clip arms do not reduce the size of the clear opening of the clip vis-à-vis the clear opening of the applicator, as is the case with the clips known in the art. In the clips of the known configuration having a tangent angle of 90° at the distal ends of the clip arms and at least one break location per clip limb, the force is passed into the clip from the applicator substantially at the break locations, the distal ends detach and depart thereby from the limbs of the clip applicator toward the inside and make sure that the distance of the distal ends of the clip arms becomes considerably smaller than the distance of the two limbs of the clip applicator. This can lead to a slightly pressed clip becoming unable to accommodate a piece of tissue because the tissue gets caught at one or both distal ends of the clip of the known configuration. Using the above embodiment makes sure that also a slightly pressed clip can still accommodate the tissue to be seized without damaging it (e.g. without piercing it with the relatively acuate shaped distal end of the clip).

According to another advantageous embodiment of the invention, the clip arm in the plane of the surgical clip is from its distal end to its proximal end so formed that a first derivation of the curvature of the neutral fiber of the clip arm has no change of sign in the region of a length on the clip arm of 8% to 100%. This means that the form of the clip arm does not change from convex to concave throughout this entire region. This configuration provides for a particularly uniform distribution of the pressing force in the compressed clip over the entire clip length.

According to again another advantageous embodiment of the invention, at least two pairs of clip arms are provided, wherein a clip arm of one pair of clip arms is at its distal end connected with at least a distal end of another clip arm of another pair of clip arms, and forms a distal connection portion. This means that a double rack clip or a plural rack clip is formed in which the individual clip arm pairs are respectively connected with each other at the distal ends of the clip arms. Such clips are frequently formed as ring clips, double ring clips and plural ring clips, respectively, by forming them from e.g. a sheet metal, for example by stamping or laser cutting. Single rack clips, i.e. clips having exactly one pair of clip arms, are however normally shaped from a wire that is cut to a predetermined length and then bent. It is however also possible to first bend the wire and to then cut it to length.

According to still another advantageous embodiment of the invention, the clip has two and three, respectively, pairs of clip arms, and the clip is formed into an open or closed ring clip or double ring clip, preferably by means of stamping, laser sintering, rolling, casting, metal inject molding and/or cutting, in particular laser cutting or water jet cutting. A closed ring clip, double ring clip or also plural ring clip is a clip wherein two adjacent pairs of clip arms respectively form a closed ring. Accordingly, an open ring clip, a double ring clip or also a plural ring clip is a clip in which two neighboring pairs of clip arms respectively form a ring which is discontinuous at one point. This can be advantageous if one wishes to compress tissue which has, in the compressed state, considerably different thickness in regions located close to each other. Using an open ring clip, each pair of clip arms can then be compressed so far that the optimum compression of the tissue is achieved.

According to a further advantageous embodiment of the invention, a recess is provided in the region of the distal end of a clip arm and/or a distal connection portion which is open in the proximal direction and closed in the distal direction so that the recess is proximally accessible and forms a first abutment face in the distal direction and preferably forms a second abutment face in the lateral direction. Thereby, the recess is further preferably made by means of stamping and/or punching. With a first abutment face at the distal end of the clip, a co-operation with a corresponding projection at a limb of a clip applicator can be achieved which prevents a clip from being pushed by the tissue toward proximal and out of the jaw of the clip applicator when it is slid onto the tissue to be seized. This means that this abutment face makes sure that the clip is held at the proper position in the jaw of a clip applicator. Otherwise it can happen that the tissue to be seized shifts the clip vis-à-vis the jaw of the clip applicator toward proximal because the clip comes into abutment against the tissue in for example the region of the clip throat, and the clip applicator is moved farther toward distal by the user but the tissue does not sufficiently give way to this displacement.

If further a second abutment face is additionally provided toward lateral, the clip can co-operate with the limbs of the clip applicator in such a manner that an active opening of the clip beyond the relaxed, i.e. substantially stress-relieved, form of the clip can be effected. If the jaw of the clip applicator is controlled, i.e. opened and closed, by means of cranks, cranks can be provided that, in a closing operation of the yaw of the clip applicator, that is a process of compressing the clip, initially open the jaw of the clip applicator by a certain amount before it is subsequently closed to thereby compress the clip. In order for the clip to follow this initial opening movement without falling out of the jaw of the clip applicator, and for this to also effect an enlargement of the clear opening width of the clip, there are two possibilities. On the one hand, the clip can be compressed elastically before it is introduced into the magazine of the clip applicator so that it is elastically biased in the initial position of the jaw of the clip applicator. It can already be present in the magazine of the clip applicator under an elastic pre-stress and is so introduced into the jaw of the clip applicator. However, the clip can be elastically compressed not until it is fed forward into the jaw part of the clip applicator and be biased thereby, for example via a feed channel narrowing in the cross direction of the clip. If now the jaw of the clip applicator widens, i.e. opens, the clip relieves tension and the clip arms respectively follow the opening movement of the limbs. If, however, a clip is fed into a magazine of the clip applicator while being pre-stressed, its friction during the clip transport is considerably higher than in a relieved clip, which is in turn disadvantageous in the dimensioning of the components involved with the feeder. Another option resides in actively widening the clip, wherein the limbs engage into the clip arms laterally from the outside and, with the opening movement of the jaw, actively draw them toward lateral. In both cases, a clip opening can be achieved for which an applicator having a larger diameter would have to be used according to the prior art. In particular in endoscopic clip applicators, it is however always advantageous to use a clip applicator having a smaller diameter because then smaller incisions are required which results in quicker cure thereof and in lesser scarring. If it is referred to a diameter of a clip applicator herein, this refers to the shaft diameter and not to its handle.

According to still another advantageous embodiment of the invention, the recess is formed in a distal connection region of two distally connected clip arms, preferably by forming the sectional dimensions of the distal connection region on the proximal and/or medial side of the clip arm, wherein a reduction of the sectional dimension is effected preferably in the distal and/or the lateral direction, wherein further preferably a tapering is effected to substantially half the sectional dimension. When this recess is arranged in a distal region of the clip arms, a smaller force is required to widen the clip. In this case, the limbs of the jaw of the clip applicator may be formed not that massive, which is advantageous to the overall slim structure of the clip applicator. Alternatively to the provision of a recess in the clip arms, the abutment faces may also be formed by projections provided at the clip arms. The recess solely allows for a more simple and cost-efficient provision of the respective abutment faces.

According to a still further advantageous embodiment of the invention, a proximal connection region of two clip arms, one clip arm and/or if need be a distal connection portion of two clip arms have a variable height and/or width in at least one direction perpendicular to the neutral fiber, preferably of at least ±10%. Because the connection regions of the clip arms do not essentially contribute to a stability of the compression, they may, for example, be formed thinner.

According to again another advantageous embodiment of the invention, the sectional area of a clip arm and/or a proximal connection region increases toward the clip throat, while the clear opening does not decrease at the decisive distal end, wherein in particular the width of the clip arm and/or the proximal connection region varies increases. In the compressed state of the clip, the largest side loads prevail in the region of the clip throat so that an increase of the cross-section in this region can increase the closing force of the clip without lowering the clear opening of the clip at the distal end.

According to still another advantageous embodiment of the invention, at least one clip arm has at least a portion having a wave form and/or a zigzag form in a direction parallel and/or perpendicular to the clip plane. With this configuration, the position of the clip on the tissue can be secured even better, and a gliding off of the seized tissue can be made further difficult.

According to a further advantageous embodiment of the invention, a pair of clip arms has clip arms that are tapered from a lateral direction, preferably by means of an enlarged radius at the outer edge of the clip arm. This tapering of the clip arms is not required to extend over substantially the entire length of the respective clip arm but may, in an advantageous manner, be provided in only a predetermined region. This configuration is advantageous when a clip is accommodated in an extremely small dimensioned shaft of an endoscopic clip applicator. In this case, a clip magazine can be set-up so that the clip pierces the outer wall of the shaft, for example in a slot, and thus forms a part of the outer wall of the shaft itself. Thereby, it is advantageous when the clip (at least the respective region of the clip) forms a uniform surface with the skin surface of the shaft.

According to another advantageous embodiment of the invention, at least one clip arm has a profile at its inside area which is formed preferably by punching, rolling or cutting. Further preferably, an atraumatic profile is provided. With such a profile, in particular the position of the clip along the longitudinal axis of a hollow organ can be further secured.

According to still another advantageous embodiment of the invention, the clip arms of a pair of clip arms, and preferably also the clip arms of different pairs of clip arms, are formed substantially uniformly. In this manner, the position of the clips need not be paid attention to upon feeding them into a magazine of a clip applicator. Alternatively, plural pairs of clip arms of a clip may be different also between each other. For example, in a clip having three pairs of clip arms, the middle pair of clip arms can consist of two corrugated clip arms, wherein the two outer pairs of clip arms consist of straight clip arms. The configuration of the individual pairs of clip arms may be arbitrary, and also the clip arms of a pair of clip arms may be uniform or diversified.

According to another aspect of the invention, a method of manufacturing one of the above-described surgical clips includes the following steps. Stamping a blank out of a sheet metal, wherein the blank is kept connected to the remaining sheet metal at at least one position, preferably in the region of the future clip throat. Subsequent bending the blank in a direction perpendicular to the remaining sheet metal so that the clip arms project from the sheet metal plane and a surgical clip is formed thereby, wherein such bending can be effected in plural steps. Finally, the clip is separated from the remaining sheet metal. With such a method, the above-described clips can be manufactured cost-effectively and securely. By separating the clips from the remaining sheet metal only at the end of the method, they cannot get lost during the production process and cannot block or damage a machine, for example. In the above-described method, a different separating method can be used instead of the stamping method, as is e.g. described above, and the separation can be effected by means of stamping. The different designation here mainly serves the unambiguous identification of the individual method steps in the further description.

According to a further aspect of the invention, an alternative method of manufacturing a previously described surgical clip includes the following steps. Stamping a blank out of a sheet metal, wherein the blank does not maintain any material connection to the remaining sheet metal. Next, clamping the blank into the remaining sheet metal in the region in which the blank has been stamped out of the sheet metal. Subsequent bending the blank in a direction perpendicular to the remaining sheet metal so that the clip arms project from the sheet metal plane and a surgical clip is formed thereby, wherein such bending can be effected in plural steps. Finally, the clip is taken out of the remaining sheet metal. This method requires a very precise stamping of the clip blank from the sheet metal. In return, however, a second stamping or the like and a corresponding process step are no longer required. The completed clips can be pressed, shaken or otherwise be taken out of the sheet metal.

According to an advantageous embodiment of the above-described manufacturing methods, a step of punching of a profile on at least one side of the sheet metal prior to and/or after the stamping of the blank is carried out, wherein the punching can be performed in plural steps.

BRIEF DESCRIPTION OF THE DRAWING FIGURES

Further advantages and features of the invention become apparent to the skilled person from the attached figures and the detailed description of the embodiments.

DETAILED DESCRIPTION

Hereinafter, the embodiments of the various aspects of the invention will be described with reference to the drawings.

Referring to FIGS. 1 to 7, a first embodiment of the first aspect of the invention will subsequently be described in detail.

Figure 1:
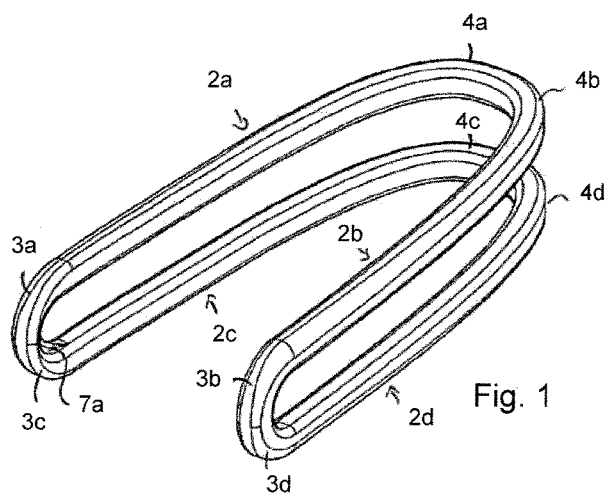
FIG. 1 shows a perspective view of a double rack clip and a ring clip, respectively, according to a first embodiment.
Figure 2:
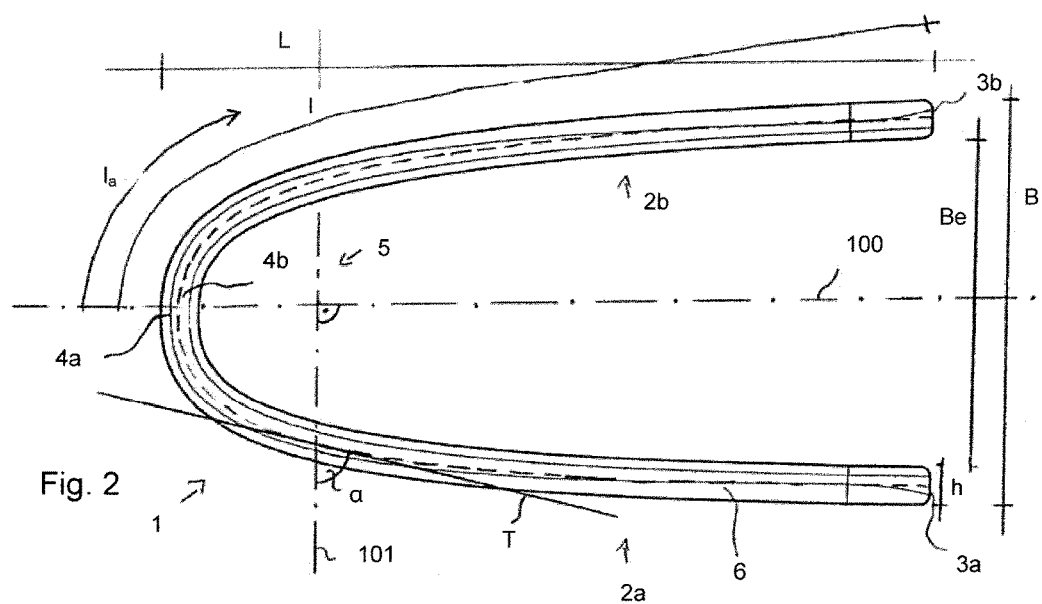
FIG. 2 shows a top view of the double rack clip according to FIG. 1.
Figure 3:
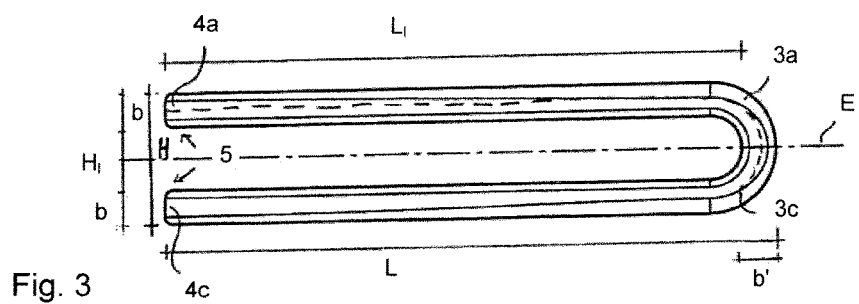
FIG. 3 shows a side view of the double rack clip according to FIG. 1.
Figure 4:
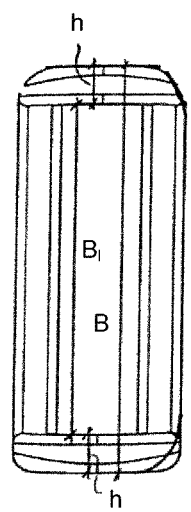
FIG. 4 shows a front (distal) view of the double rack clip according to FIG. 1.
Figure 5:
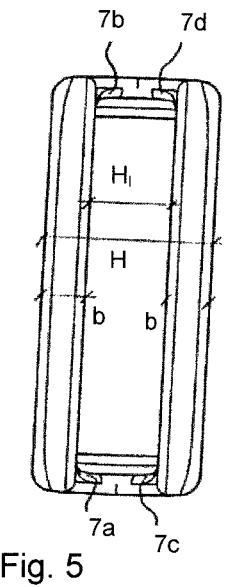
FIG. 5 shows a rear (proximal) view of the double rack clip according to FIG. 1.
Figure 6:
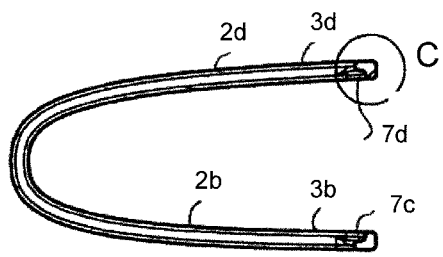
FIG. 6 shows a sectional view of the double rack clip according to FIG. 1 through a symmetry plane of the double rack clip.

The surgical clip 1 shown in FIGS. 1 to 7 is suitable for use with a surgical clip applicator, in particular with a surgical clip applicator of the multi-fire kind, and further preferably for such a clip applicator in single use. The clip 1 has two pairs of clip arms 2a, 2b, 2c, 2d, wherein each clip arm 2a, 2b, 2c, 2d has a distal end 3a, 3b, 3c, 3d and a proximal end 4a, 4b, 4c, 4d. The two clip arms 2a, 2b bzw. 2c, 2d of each pair of clip arms are connected to each other at their proximal ends 4a, 4b and 4c, 4d, respectively, and so form two clip throats 5 in total. As shown in FIG. 2, a tangent angle α between a tangent T to a neutral fiber 6 of a clip arm 2a, 2b, 2c, 2d and a vertical 101 onto a longitudinal axis 100 of the clip 1 over the entire length 1 of the clip arm 2a, 2b, 2c, 2d increases continuously.

The length of the clip L is determined by the vertical projection of the clip arms 2a, 2b, 2c, 2d onto the longitudinal axis 100 of the clip. The longitudinal axis 100 of the clip 1 is in this embodiment also a line of intersection of two orthogonally intersecting symmetry planes (mirror symmetry) of the clip 1. The length 1 of a clip arm 2a corresponds to the unwinding of the clip arm 2a to a straight. The position on a clip arm 2a is represented by the length $l_a$, wherein $l_a$ is 0 in the region of the clip throat (i.e. at the proximal end of the clip 1) and 1 at the distal end of the clip 1. The height h of a clip arm 2a, 2b, 2c, 2d is determined by the thickness of the raw material from which it is mostly formed. The width b of a clip arm 2a, 2b, 2c, 2d is determined by the form carved out, i.e. stamped out, for example, of the raw material. The height H and the width B of the clip 1 however depends not only from the raw material, from which it is usually made, but also from how the blank R made from the raw material is formed.

Hence, the following interrelations result:

$$B = B_1 + 2h; \qquad \qquad 1)$$

$$H = H_1 + 2b; \qquad \qquad 2)$$

wherein $H_1$ is the clear height and $B_1$ is the clear width of the clip 1. Between a predetermined position, i.e. at a length on (the) clip arm $l_a$, an angle α spans between a tangent to the neutral fiber 6 of a clip arm 2a and a vertical 101 onto the longitudinal axis 100 of the clip 1. In the present embodiment, the tangent angle α has a value of about 25° on a length on the clip arm $l_a$ of 6%, a value of about 60° on a length on the clip arm of 15%, and a value of about 75° in a length on the clip arm of 27%. Besides, the tangent angle α has a value of substantially 0° on a length on the clip arm $l_a$ of about 0% (i.e. in the clip throat 5 where the clip arms 2a, 2b are connected and intersect the longitudinal axis 100 in FIG. 2). At the distal end of the clip 1, i.e. at a length on the clip arm $l_a$ of 100%, the tangent angle α has a value of about 84°. The deviations of the clips from these nominal dimensions range between ±2°, preferably ±1°.

The clip arms 2a, 2b, 2c, 2d of the clip 1 of this embodiment are, in the plane of the clip 1 from their distal end 3a, 3b, 3c, 3d to their proximal end 4a, 4b, 4c, 4d, so formed that a first derivation of the curvature of the neutral fiber 6 of the clip arm 2a, 2b, 2c, 2d has no change of sign. This means that no break point is provided in the clip arm where the tangent angle α changes substantially erratically. The clip arms 2a, 2c are connected at their distal ends 3a, 3c and form a connection portion 11, and the clip arms 2b, 2d are connected at their distal ends 3b, 3d and form a connection portion 12. The clip 1 of this embodiment hast two pairs of clip arms and is formed as a closed ring clip. This clip 1 is stamped out of a sheet metal which can be sourced on a roll. Normally, two of such ring clips are stamped out of the sheet metal side by side.

Figure 7:
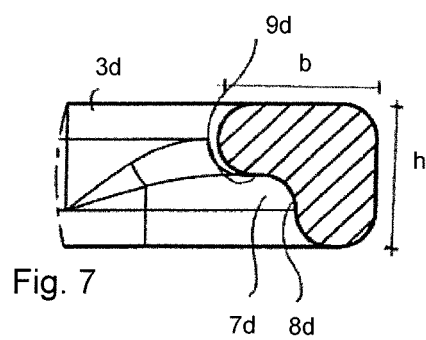
FIG. 7 shows a magnification of a detail C in FIG. 6.

FIG. 7 shows a cross-section through a distal region 3d of the clip arm 2d in detail. There, a recess 7d is formed in the connection portion 12 which is proximally, or toward the proximal side, open and distally, or toward the distal side, closed. Thereby, the recess 7d is accessible from the proximal side and open from the medial side, and forms a second abutment face 8d toward lateral. Besides, the recess 7d is open from the medial side and forms a second abutment face 9d toward lateral. In this embodiment, the recess 7d is formed concurrently with the stamping operation. Alternatively, the recess 7d can also be formed by punching the sheet metal prior to stamping out the blank R, or by punching the blank R after the stamping operation. This is independent of the manufacturing methods described below, according to which the clip is manufactured.

The recess is formed by tapering the cross-sectional dimensions b, h of the distal connection portion 11, 12 toward distal and toward lateral, wherein the tapering is effected substantially onto half the cross-sectional dimension b, h.

In the clip according to this embodiment, both the height h, h' of the sheet metal, and thus that of the clip arms 2a, 2b, 2c, 2d, and the width b, b', b" thereof over the entire length 1 of the clip arms 2a, 2bn, 2c, 2d are invariable. Besides, this clip 1 has neither a corrugated form not a zigzag form in a direction parallel and/or perpendicular to the clip plane E. Also, this clip 1 has no clip arms 2c, 2d that are tapered from a lateral side, as these are advantageous when in this clip 1 these clip arms 2c, 2d project laterally from the shaft of a clip applicator, or at least pierce the shaft wall. Further, the clip 1 of this embodiment has no profile at its clip arms 2a, 2b, 2c, 2d. The clip of this embodiment is designed such that a first derivation of the curvature of a neutral fiber of the clip arm 2a, 2b exhibits a change of sign in the region of a length on clip arm $l_a$ of 6.3%. The first derivation of the curvature of the neutral fiber does not exhibit any further changes of sign.

Figure 19:
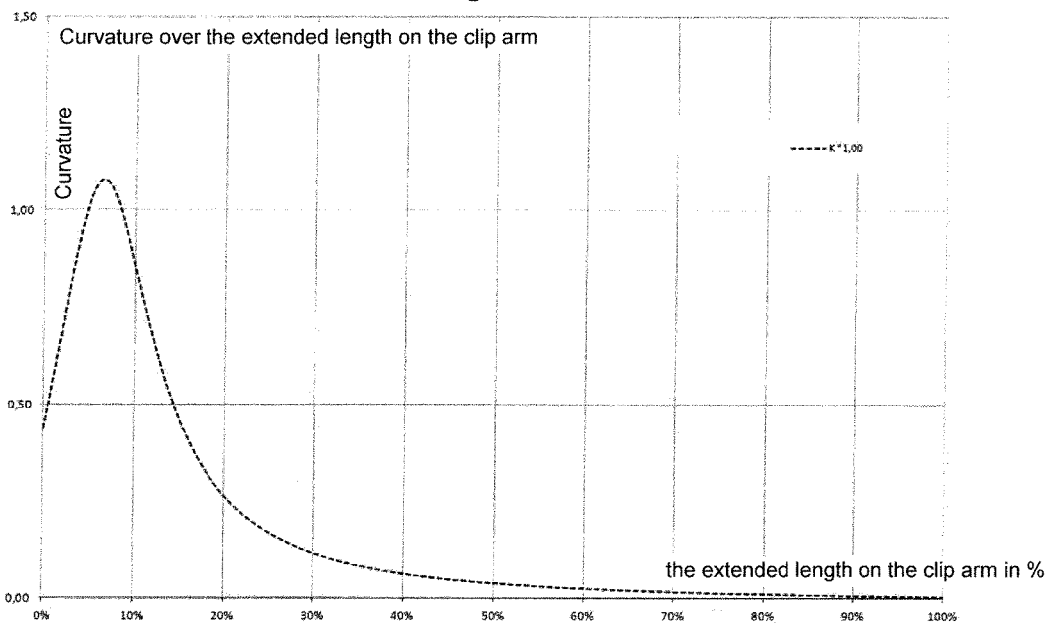
FIG. 19 shows a diagram illustrating the curvature of a clip bracket over the length on the clip arm according to an embodiment.
Figure 20:
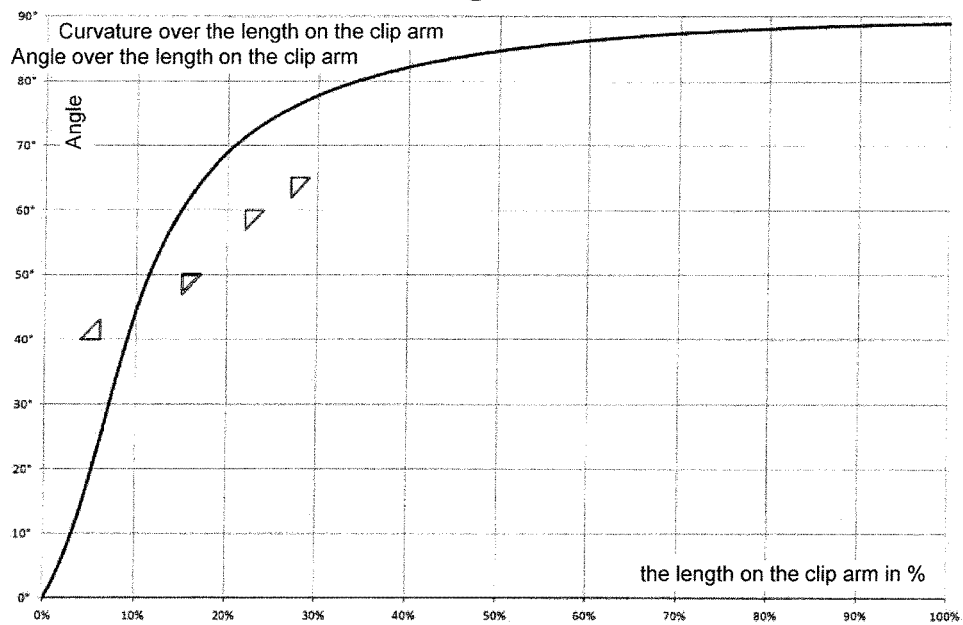
FIG. 20 shows a diagram illustrating the angle between the clip bracket and a vertical onto the clip axis over the length on the clip arm according to an embodiment.

In FIG. 19, the development of the curvature of the neutral fiber of a clip arm of this clip over the length on the clip arm is shown. Here, the length on the clip arm is illustrated percentally relative to the clip arm length. Correspondingly, FIG. 20 shows the angle a tangent to the neutral fiber of the clip of this embodiment takes, or draws, with a straight which stands vertically on the clip axis. Also here, the length on the clip arm is illustrated percentally relative to the clip arm length. The additionally illustrated triangles define points and, thus, a corridor in which the graph must take course in order to obtain an advantageous clip according to this invention.

Figure 12:
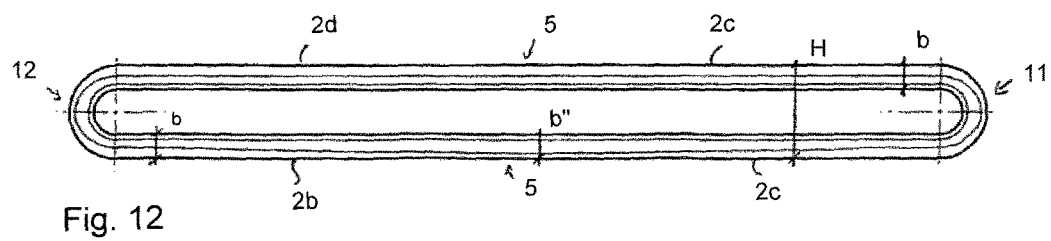
FIG. 12 shows a bottom view of the blank of a double rack clip after a stamping operation according to a second embodiment.
Figure 13:
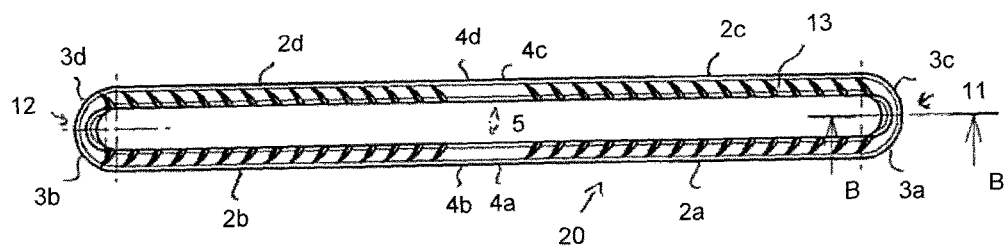
FIG. 13 shows a top view of a blank of a double rack clip according to FIG. 12 after a stamping operation and a punching operation.
Figure 14:
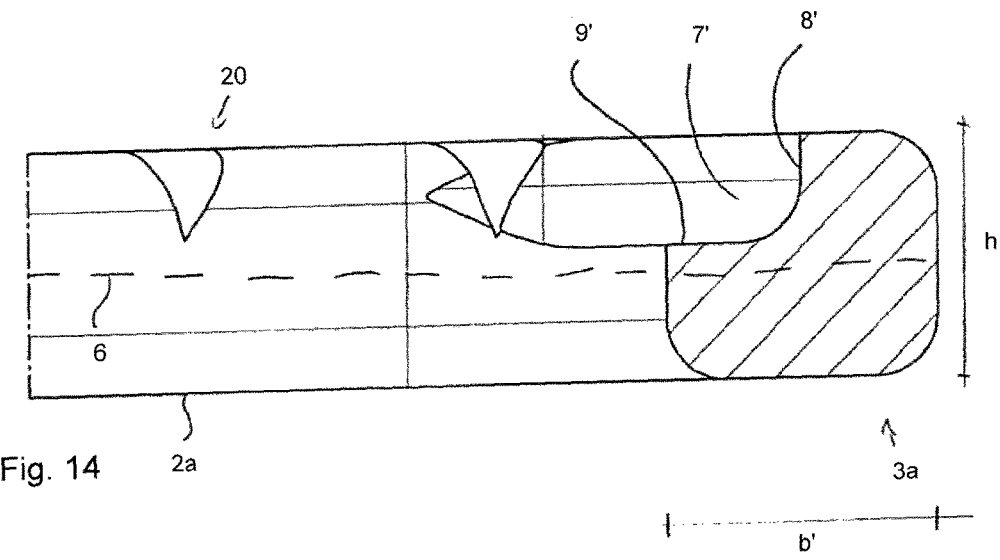
FIG. 14 shows a view of the blank according to FIG. 13 along the line B-B.

A second embodiment of the clip 1 according to the invention is shown in FIGS. 12 to 14. In the following, only the differences to the first embodiment are described. As can in particular be seen from FIG. 13, the clip 1 has a profile at the inner surface 13 of the clip arms 2a, 2b, 2c, 2d, wherein no profile is provided in the region of the clip throat 5 to be formed. Alternatively, a profile can be provided also in the region of the clip throat 5, or regions can be provided at one or more clip arms 2a, 2b, 2c, 2d in which no profile is provided. This profile is formed by punching, or embossing, wherein the sheet metal has been punched before the blank R has been stamped out therefrom. In the present case, the profile has been applied onto and into, respectively, the metal strip using an embossing roller. It is also possible to emboss the metal strip using a swing punch, however the use of an embossing roller facilitates the creation of seamless and non-overlapping impressions. The profile of this clip consists of slot-shaped indentations 20 which are arranged substantially parallel to each other on a clip arm 2a, 2b, 2c, 2d. The recess 7' was not formed upon stamping the blank R but has been milled after the stamping of the clip 1. In this manner, the abutment faces 8', 9' can be formed with sharper edges so that the remaining height h and width b' of the clip arm 2a, 2d can be larger for abutment faces 8', 9' which are comparable in size to the abutment faces 8d, 9d of the first embodiment. In addition, the width b' of the distal regions 3a, 3b, 3c, 3d of the clip arms 2a, 2b, 2c, 2d are in this embodiment slightly smaller than the width b of the proximal regions 4a, 4b, 4c, 4d thereof. In particular, the connection portions 11, 12 are formed so at to have a smaller width b'.

Figure 8:
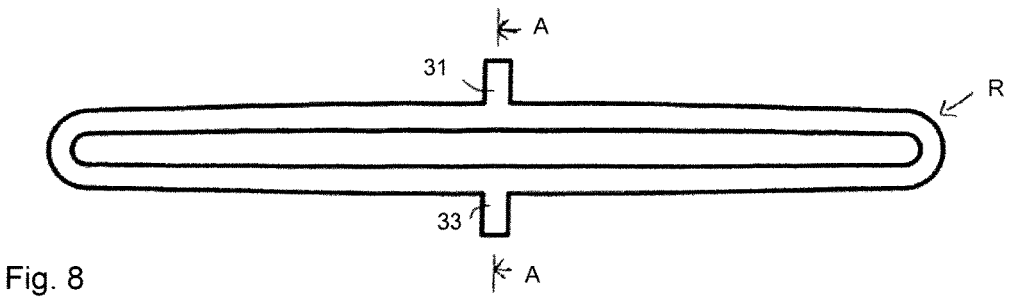
FIG. 8 shows a top view of a blank of a double rack clip after a stamping operation and prior to a bending operation and a separating operation.
Figure 10:
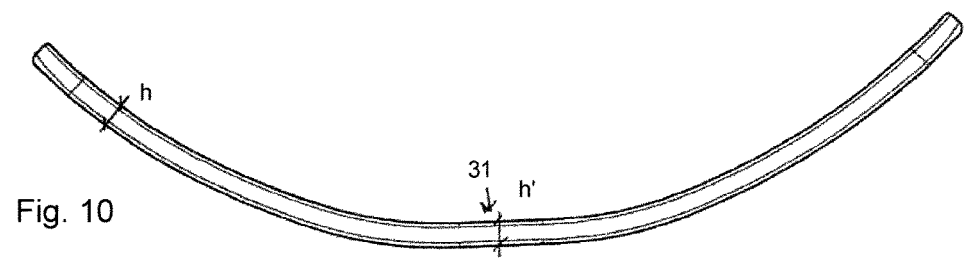
FIG. 10 shows a side view of the blank according to FIG. 8 after a first bending operation.
Figure 9:
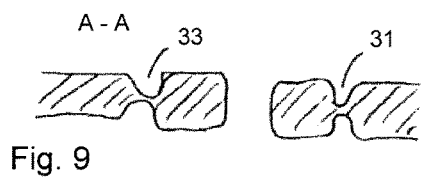
FIG. 9 shows a view of the blank according to FIG. 8 along the line A-A.
Figure 11:
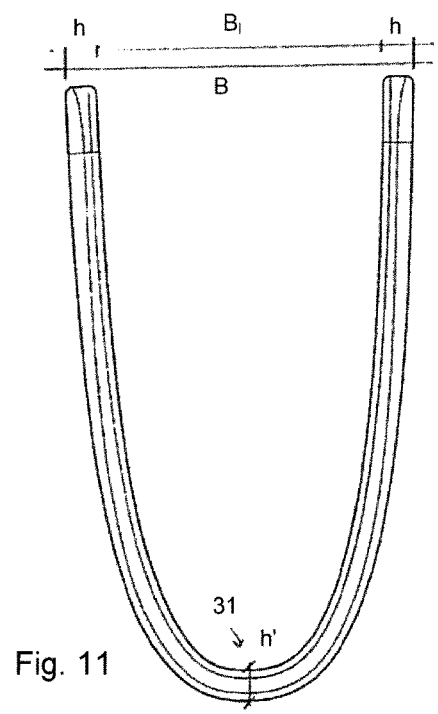
FIG. 11 shows a side view of the blank according to FIG. 8 after a second bending operation.

As is already indicated previously, the present double rack clip 1 is made out of a metal strip, wherein two clips are simultaneously formed side by side from the metal strip. Initially, the metal strip is unwound from a roll. In a first process step, a profile is embossed into the future inner surface of the clip 1 using an embossing roller. Then, the rough form of the future clip 1 is stamped out of the sheet metal, and the blank R is formed thereby. Thereby, as shown in FIG. 8, the blank R stays connected to the sheet metal (not shown) at two locations 31, 33. However, the thickness of the sheet metal is strongly reduced at the connection points 31, 33 (cf. FIG. 9) so that later the clip 1 can be separated from the remaining sheet metal more easily. Now the blank R is bent out of the sheet metal plane. In this embodiment, the bending is performed in two steps. After a first bending step, the blank R has the form shown in FIG. 10. The remaining sheet metal is not shown in FIGS. 10 and 11. By means of a second bending step, the blank R takes the form shown in FIG. 11. Finally, the connection points 31, 33 are cut in a separating step, and thereby the blank R and the now completed clip 1, respectively, is separated from the remaining sheet metal. The separating is performed by stamping the connection points 31, 33.

Figure 15:
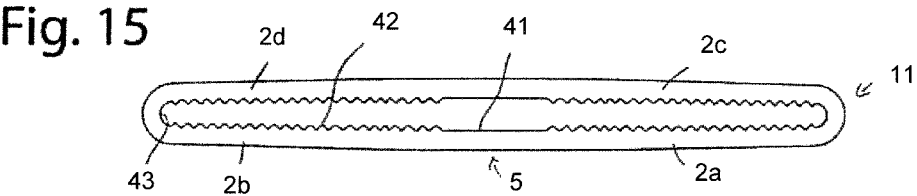
FIG. 15 shows a blank having a variable inner contour.
Figure 16:
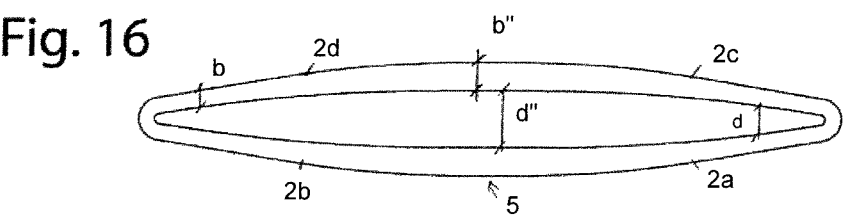
FIG. 16 shows a blank having a variable width over the length of the clip arms.
Figure 17:
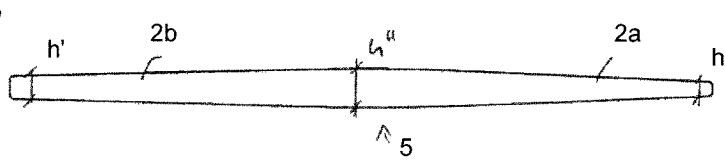
FIG. 17 shows a blank having a variable height over the length of the clip arms.

In the following, further embodiments and modifications of the clip will be described. FIG. 15 shows a blank of a clip corresponding to FIGS. 12 and/or 13 with a variable inner contour 42. This wavelike inner contour 42 of the clip arms 2a, 2b, 2c, 2d additionally secures the clip against a shifting of the clip on the vessel in the direction of the clip axis 100. The wavelike inner contour 42 can also be formed in the region of the clip throat 5, wherein preferably no variable inner contour 41 is provided in the clip throat 5 in order not to generate any stress peaks during the compression which, as the case may be, might provoke a brittle fracture of the material. Preferably, a non-contoured inner side 43 of the clip brackets is also provided in the region of the distal connection of two clip arms. As shown in FIG. 15, the waves of the contour can exhibit a variable wavelength. In addition, the transition from a non-waved inner contour in the region of the clip throat 5 to a waved inner contour can be formed with a gradually increasing wave amplitude. In FIG. 16, the blank of a clip is shown in which the width b of a clip bracket decreases from the clip throat 5 toward the distal end of the clip bracket. In the region of the clip throat 5, the clip bracket has the width b". In addition, the distance of the two clip brackets 2a, 2c and 2c, 2d, respectively, facing each other changes from the clip throat 5 to the distal end of the clip. In the region of the clip throat 5, this embodiment exhibits the distance d". FIG. 17 shows a blank of a clip according to e.g. FIG. 15 or 16 in a side view. In a clip of this kind, the height of the raw material is variable to that clips having a variable clip arm height h can be formed. In the present embodiment, the clip arm 2a has the height h at its distal ends, whereas the clip arm 2b has the height h' at its distal end. In the region of the clip throat 5, both clip arms 2a, 2b have the height h".

Figure 18:
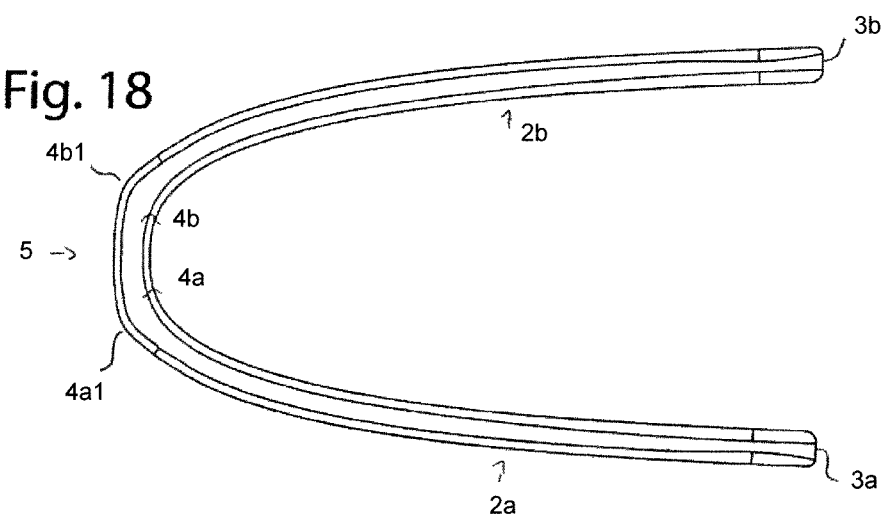
FIG. 18 shows a clip having compression humps.

FIG. 18 shows a modification of the clip according to FIG. 2, wherein a compression hump 4a1, 4b1 is formed in the region of the proximal portions 4a, 4b of the clip arms 2a, 2b, i.e. in the vicinity of the clip throat 5. These compression humps facilitate the compression of the clip at a time when the clip is already almost completely compressed. More specifically, these compression humps help in pressing the eye which forms upon the compression of the clip in the region of the clip throat 5 to be small. In the region of the eye, no tissue can be seized. Hence, a clip eye as small as possible must be striven for.

The features of the various embodiments are suitably combinable at will. In addition, numerous modifications and variations unfold within the scope of the claims.

For instance, the clip can also be manufactured by means of die sinking. This technique can be employed both in place of the milling and in place of the punching in the corresponding method steps.

The invention claimed is:

1. A surgical clip for a surgical clip applicator, the surgical clip comprising:
   at least one pair of clip arms, wherein each clip arm has a distal end and a proximal end, the clip arms connected to each other at their proximal ends to form a clip throat,
   a tangent angle between a tangent to a neutral fiber of at least one clip arm and a perpendicular to a longitudinal axis of the surgical clip increases over an entire length of said at least one clip arm substantially continuously,
   wherein the tangent angle has, on a length on said at least one clip arm of 22%, a value of at least 60°.

2. A surgical clip as claimed in claim 1,
wherein
the tangent angle has, on a length on said at least one clip arm of 6%, a value not exceeding 40°.

3. A surgical clip as claimed in claim 1,
wherein
the tangent angle has, on a length on said at least one clip arm of 15%, a value of at least 50°.

4. A surgical clip as claimed in claim 1,
wherein
the tangent angle has, on a length on said at least one clip arm of 22%, a value of at least 60°.

5. A surgical clip as claimed in claim 1,
wherein
the tangent angle has, on a length on said at least one clip arm of 27%, a value of at least 65°.

6. A surgical clip as claimed in claim 1,
wherein
the tangent angle has, on a length on said at least one clip arm of 100%, a value not exceeding 88°.

7. A surgical clip as claimed in claim 1,
wherein
a first derivation of a curvature of the neutral fiber of said at least one clip arm has no change of sign in a region of a length on said at least one clip arm of 8% to 100%.

8. A surgical clip as claimed in claim 1,
wherein
the at least one pair of clip arms comprises at least two pairs of clip arms are provided, and wherein a clip arm of one of said at least two pairs of clip arms is at its distal end connected with at least a distal end of a clip arm of another of said at least two pairs of clip arms, and forms a distal connection portion.

9. A surgical clip as claimed in claim 8,
wherein
the surgical clip has two and three, respectively, pairs of clip arms, and the surgical clip is formed into an open or closed ring clip or double ring clip, by means of stamping, laser sintering, rolling, casting, metal inject molding and/or cutting.

10. A surgical clip as claimed in claim 1,
wherein
a recess is provided in a region of the distal end of said at least one clip arm and/or a distal connection portion which is open in a proximal direction and closed in a distal direction so that the recess is proximally accessible and forms a first abutment face in the distal direction and forms a second abutment face in the lateral direction or the medial direction, wherein the recess is further made by stamping and/or punching.

11. A surgical clip as claimed in claim 10,
wherein
the recess is formed in a distal connection region of two distally connected clip arms by forming sectional dimensions of the distal connection region on the proximal and/or medial side of each of said two distally connected clip arms, wherein a reduction of a sectional dimension is effected in the distal and/or the lateral direction, wherein further a tapering is effected to substantially half the sectional dimension.

12. A surgical clip as claimed in claim 1,
wherein
a proximal connection region of two clip arms, one clip arm and/or a distal connection portion of two clip arms have a variable height and/or width at least one direction perpendicular to the neutral fiber.

13. A surgical clip as claimed in claim 1,
wherein
a sectional area of said at least one clip arm and/or a proximal connection region vary toward the clip throat, wherein a width of said at least one clip arm and/or the proximal connection region varies.

14. A surgical clip as claimed in one of claim 1,
wherein
said at least one clip arm has at least a portion having a wave form and/or a zigzag form in a direction parallel and/or perpendicular to a clip plane.

15. A surgical clip as claimed in one of claim 1,
wherein
said at least one pair of clip arms are varied in cross-section from a lateral direction a chamfer in a distal region of said at least one pair of clip arms.

16. A surgical clip as claimed in claim 1,
wherein
said at least one clip arm has a profile at its inside area which is formed by punching, rolling, cutting, wire-electro discharge machining or ram electrical discharge machining.

* * * * *